(12) United States Patent
Karapetyan

(10) Patent No.: US 7,118,378 B1
(45) Date of Patent: Oct. 10, 2006

(54) APPARATUS FOR DENTAL IMPLANT TREATMENT

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 0 days.

(21) Appl. No.: 11/085,411

(22) Filed: Mar. 21, 2005

(51) Int. Cl.
*A61C 5/04* (2006.01)

(52) U.S. Cl. ........................................ 433/90; 604/181
(58) Field of Classification Search ................. 433/89, 433/90; 604/181; 606/92, 93
See application file for complete search history.

(56) References Cited

U.S. PATENT DOCUMENTS

| 833,044 | A | * | 10/1906 | Goodhugh | 433/90 |
| 4,801,263 | A | * | 1/1989 | Clark | 433/90 |
| 6,325,627 | B1 | | 12/2001 | Ashman | |
| 6,736,799 | B1 | * | 5/2004 | Erbe et al. | 604/181 |

* cited by examiner

*Primary Examiner*—Melba Bumgarner

(57) ABSTRACT

An improved apparatus for dental implant treatment includes a syringe comprising a barrel portion including a slightly bended cylinder in the area of the syringing side of the barrel and comprising a perpendicularly extended rim at its another side. Also, the improved apparatus for dental implant treatment comprises a piston member rigidly connected to the connecting rod at the syringing side and handle member extended from the connecting rod's another side. The connecting rod at the handle side portion includes the threaded portion with the outer thread appropriate to the inner thread of the controlling means of the adjustment means. The improved apparatus for dental implant treatment also includes the cover coupled with the syringing side of the barrel and a separate pipette providing suction of the patient's blood from the extracted tooth socket and injecting such blood into synthetic bone graft material located in the barrel.

3 Claims, 4 Drawing Sheets

APPARATUS FOR DENTAL IMPLANT TREATMENT

FIELD OF THE INVENTION

This invention relates to the dental implant treatment procedures and, more particularly, to an apparatus for installing synthetic bone graft material.

BACKGROUND OF THE INVENTION

Presently, the methods for installing synthetic bone graft material are commonly well known. Generally the known methods provide preservation of the alveolar ridge surrounding a presently extracted root socket by backfilling the socket with bone graft material and installing an implant in the root socket area either immediately before backfilling or after backfilling and a delay in which new bone is allowed to grow into the bone graft material. It is also known, that usually, the dental implant is installed apically into the root socket immediately following root extraction. The open area of the root socket surrounding the implant is then backfilled with bone graft material immediately after implant placement. The implant is mostly a threaded implant (but it can be a cylinder-type) which is usually placed about 3 mm–6 mm apically to said root socket, as it is well known from prior art. The bone graft material comprises synthetic bone alloplast (e.g. such as Bioplant.RTM. HTR.RTM.) and is hydrated using the patient's own blood obtained from the patient's bleeding extraction socket after penetration but prior to insertion of the bone graft material and the implant into said root socket. According to the another known variant, the presently extracted root socket is filled with bone graft material and primary or non-primary closure of the extraction site is performed. Bone-growth is promoted in the root socket by the bone graft material for 2–12 months. Then, after sufficient bone growth has been promoted, an implant is installed in the extraction site area in the normal manner.

In compliance with the National Survey on Oral Health conducted by the National Institute of Dental Research, over 40% of Americans over 65 years of age and about 4% of those 35 to 64 are totally edentulous. Moreover known, that those over 65 years old who still have some of their teeth have lost an average of 12 of their 28 teeth, and persons aged 55 to 64 have lost an average of 9 of their 28 teeth. Also, it is known, when an extracted or otherwise missing tooth is not replaced, atrophy of the jaw bone occurs over time. Consequently, individuals who have been partially or fully edentulous for an extended period of time are left with an atrophic alveolar ridge that can not securely support a full or partial denture or support the placement of a dental implant. The edentulous individual faces a continuing deterioration of aesthetics and a compromised ability to chew leaving the quality of the individual's oral life in an unfortunate state.

The deteriorating effect of tooth extraction on the alveolar ridge is commonly known, and it is also well known, that a tooth of a patient, comprised of a crown and root seated in the alveolar (or jaw) bone. The buccal and lingual portion of the alveolar bone is surrounded by a layer of tissue known as the gingiva or gum. The crown and root are supported by the alveolar ridge or jaw bone and the gingiva which, in the ideal case, is adjacent to the tooth at a level gum line over the underlying bone. When such a tooth or series of teeth become infected or otherwise dentally compromised such that the extraction of the crown and root are required, the root is removed from the alveolar bone by separating the surface of the root from the periodontal membrane. The portion of the alveolar bone shortly after extraction of the crown and root has bleeding clots, such that bleeding ceases and a root extraction socket remains in the alveolar bone in the shape of the extracted root. The buccal and lingual portions of the alveolar bone are composed of bone having a unique characteristic, i.e., being capable of absorbing the shocks caused by the stress movement of teeth during speech, eating, etc. The removal of a tooth and the resulting absence of frequent use pressure in the area causes the alveolar bone to shrink in that area where pressure is no longer applied (the extraction site) with the subsequent loss of 40%–60% (in a 2 to 4 year time) of the alveolar ridge's former height measured at the gum line (i.e., "disuse atrophy"). FIG. 3 shows 30 Approximately two years after the extraction of the tooth an extraction site has various degrees of loss of buccal and crestal alveolar bone. The jaw bone continues to atrophy at a bone loss rate of ½%–1% per year until death of the patient. At the modern time, the bone graft substitute material has been used to immediately fill a root extraction socket at an extraction site after a root extraction in order to promote bone growth and to avoid the expected bone atrophy (a.k.a. "Ridge Preservation"). Bone growth is promoted via the bone graft material's intermixing with the patient's own marrow blood which seeps through the root extraction socket. After some time to allow alveolar bone regeneration (approximately 1–1.5 years) dense lamina bone forms in the extraction socket area. The patient may then be considered for a denture prosthesis.

There are known some variations of the procedure, for example, inherited in the method for installing an implant in a root extraction socket and backfilling the socket area immediately after extraction (a.k.a. "immediate post-extraction implant installation"), and the method for backfilling a root extraction socket with bone graft material immediately after extraction and then delaying installation of an implant in the root extraction socket until bone graft material has promoted sufficient bone growth in the root extraction socket (a.k.a. "delayed post-extraction implant installation").

These variations are described in the U.S. Pat. No. 6,325,627, which discloses the method and apparatus for preserving the alveolar ridge around a newly extracted root socket and providing an immediate post-extraction installation of an implant by: a) immediately installing an implant in a root extraction socket following root extraction, and b) filling the remaining space in the socket with bone graft material to encourage new bone growth in the extraction site. Generally, according to an aspect of the invention, the method for preserving the alveolar ridge around a newly extracted root socket comprises the steps of installing a dental implant apically 3 mm–6 mm to the root extraction socket, filling the remaining open area of the root extraction socket with bone graft material by a syringe and retaining the bone graft material during initial healing of the bone and gingiva with a restraint such as sutures, or a collagen or a surgical foil dressing, and/or method for delayed post-extraction installation of an implant by filling the root extraction socket with bone graft material using the mentioned syringe immediately after root extraction and, after sufficient new bone growth has been promoted by the bone graft material in the root extraction socket, installing an implant in the new bone growth utilizing known methods and apparatus for installing an implant in a normal, non-atrophied jaw bone.

The apparatus of this prior art comprises the dental syringe and implant. The syringe is presented by the straight syringe HTR.RTM.-24, Item #H216102, or curved syringe HTR.RTM.-24, Item #H216112 available from Bioplant, Inc. (20 North Main Street, Norwalk, Conn. 06854), filled with 750 micron diameter HTR.RTM. to absorb blood from the bleeding root extraction socket. The syringe generally includes the handle coupled with the piston and the straight or curved cylinder with the attachable nozzle.

Another analogous syringe is described in U.S. patent application Ser. No. 08/831,941.

All known syringes are inconvenient considering non-adjustable travel/stroke of the piston inside the cylinder. Also, the known prior art includes the nozzle, which does not provide sufficient and convenient suction of the blood from the bleeding root extraction socket (i.e., the known syringes do not provide satisfied consistent of the final mixture of the sucked blood from the bleeding root extraction socket into the bottom jaw and synthetic bone graft material (e.g. such as HTR.RTM, etc.).

Thus, there is a great need in the art for the non-expensive and convenient improved apparatus for dental implant treatment, providing easy syringe's piston travel adjustment and better mixture of the patient's own blood from the bleeding root extraction socket with the synthetic bone graft material located into the syringe's cylinder.

OBJECT AND ADVANTAGES OF THE INVENTION

Accordingly, several objects and advantages of the present invention are to provide the non-expensive and convenient improved apparatus for dental implant treatment, providing easy syringe's piston travel adjustment and better mixture of the patient's own blood from the bleeding root extraction socket with the synthetic bone graft material located into the syringe's cylinder.

It is another object of the invention to provide a convenient syringe's handle.

It is still another object of the invention to provide a convenient angle of the syringe cylinder's curvature, thereby providing maximum surgeon's approachability/accessibility to the treating area.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

The known synthetic bone graft material injecting syringes do not provide possibility to adjust and/or limit the piston's travel inside the barrel.

Thus, there is a great need in the art for the non-expensive and convenient improved apparatus for dental implant treatment, providing easy syringe's piston travel adjustment and better mixture of the patient's own blood from the bleeding root extraction socket with the synthetic bone graft material.

An improved apparatus for dental implant treatment includes a syringe comprising a barrel portion including a slightly bended cylinder in the area of the syringing side of the barrel and comprising a perpendicularly extended rim at its another side. Also, the improved apparatus for dental implant treatment comprises a piston member rigidly connected to the connecting rod at the syringing side of the barrel and handle member extended from the connecting rod's another side. The connecting rod at the handle side portion includes the threaded portion with the outer thread appropriate to the inner thread of the controlling means of the adjustment means. The improved apparatus for dental implant treatment also includes the cover coupled with the syringing side of the barrel and a separate pipette providing suction of the patient's blood from the extracted tooth socket and injecting such blood into synthetic bone graft material located in the barrel.

DESCRIPTION OF THE PREFERRED EMBODIMENTS

Herein the description of an improved apparatus for dental implant treatment will be done in statics (as if the components of the improved device are suspended in the space) with the description of their relative coupling to each other. The description of the functional operations of the improved dental implant treatment will be done hereinafter.

Figure 1:
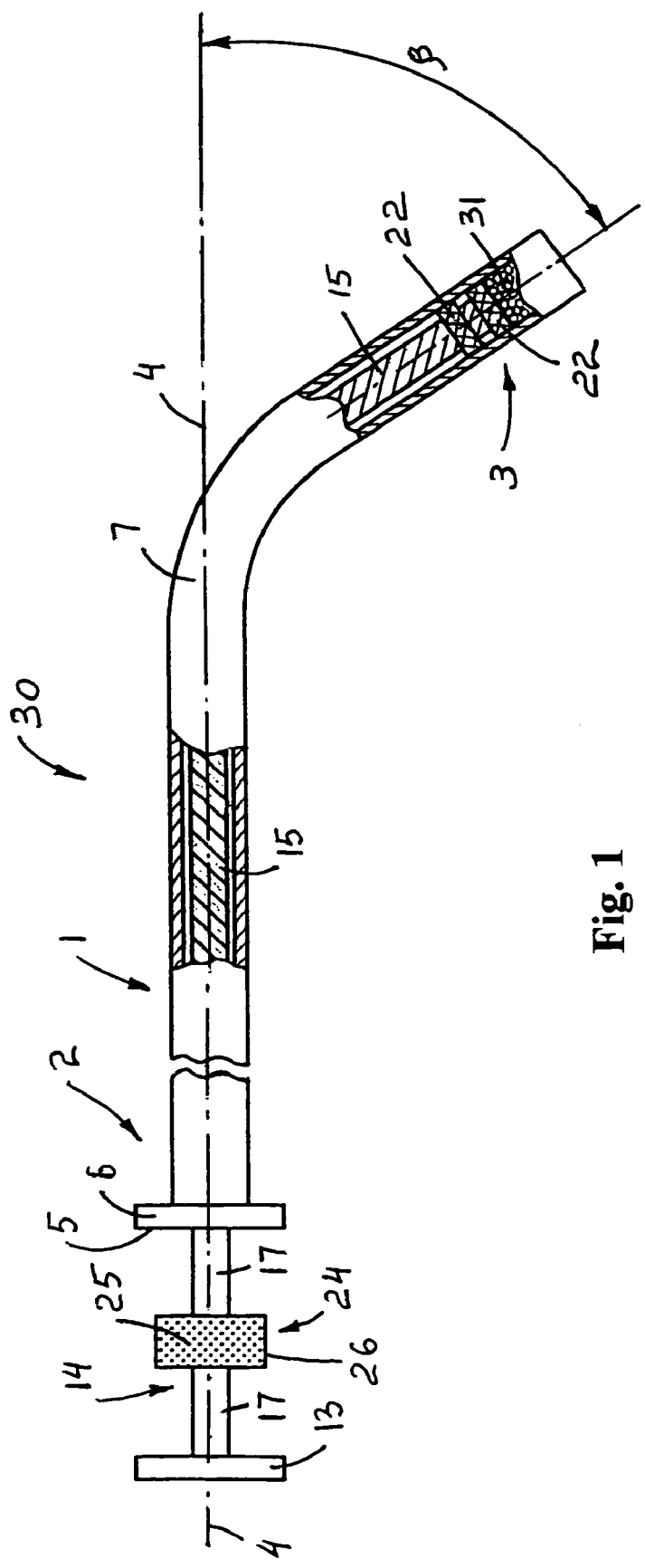
FIG. 1 is a simplified drawing of the improved syringe of the improved apparatus for dental implant treatment.

An improved apparatus for dental implant treatment (i.e. such as a barrel syringe for injection/basckfiling of the synthetic bone graft material into extracted root socket), referring to FIG. 1, includes a barrel (cylinder) portion 1 comprising a handle side portion 2 and a syringing side portion 3. The cylinder 7 of the barrel portion 1 is bended under angle "β" (relatively to the lateral axis 4) at its syringing side portion 3 of the cylinder 7. The angle "β" can approximately be 50°–70°. The barrel portion 1 can be made of any significantly reliable and non-toxic material and preferably of a transparent material. The handle side portion 2 of the cylinder 7 of the barrel portion 1 includes at its end 5 the rim 6 perpendicularly extended from cylinder 1 (the rim 6 is perpendicular to the axis 4).

Figure 2:
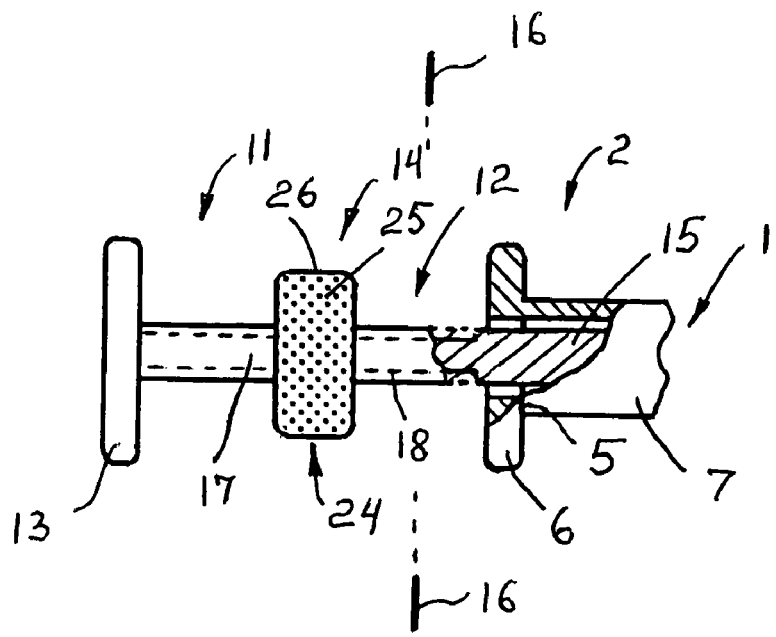
FIG. 2 is a simplified drawing of the handle portion.
Figure 3:
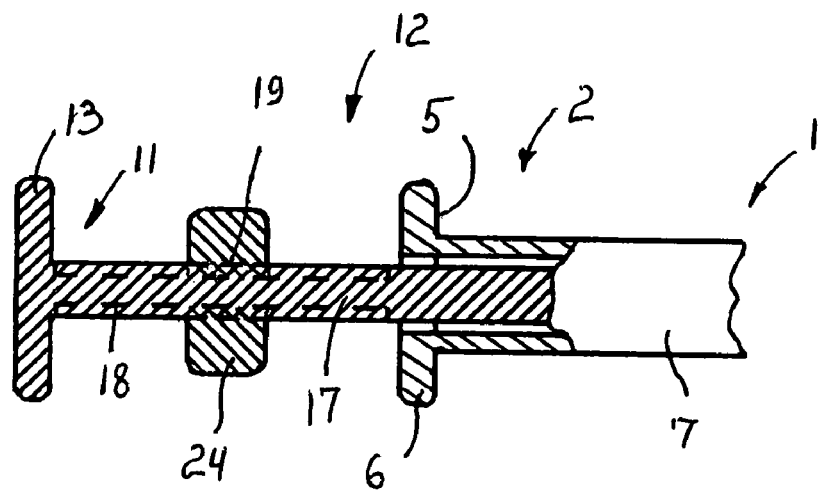
FIG. 3 is a simplified drawing of the piston portion travel adjustment means.

Also, the improved apparatus for dental implant treatment includes the piston portion 8 comprising a piston member 9 at its first end 10 appropriate to the syringing side portion 3 of the cylinder 7 of the barrel portion 1, a handle member 11 at its second end 12 appropriate to the handle side portion 2 of the cylinder 7 of the barrel portion 1. The handle member 11 includes a finger rest 13 and an adjustment means 14 providing control of the piston member 9 travel. The piston portion 8 also comprises a connecting rod 15 coupling the piston member 9 with the handle member 11. Preferably, the finger rest 13 of the handle portion 11 and connecting rod 15 can be made of solid (entire) piece (the finger rest 13 can be extended from the connecting rod 15) of a vertically flexible non-toxic material (the connecting rod 15 is bendable in the direction of the longitudinal axis 16), as it is shown in FIG. 2. The connecting rod 15 can include the threaded portion 17 with the outer thread 18. The threaded portion 17 is located at the second end 12 of the piston portion 8 (in the area of the finger rest 13). The mentioned above adjustment means 14 can for example be presented by a controlling means 24 including an appropriate inner thread 19 for coupling with the threaded portion 17 of the connecting rod 15, as it is shown in FIG. 3. The controlling means 24 can include a texture 25 on its outer surface 26 (in FIG. 3 it is conventionally/conditionally shown the controlling means in the form of a cylindrical nut (slot-nut), but controlling means 24 can be of any reasonable form/shape, configuration and size, etc.). The other types of the adjusting means and principles can be used too, for instance, a clipping principles (not shown), etc.

Figure 4A:
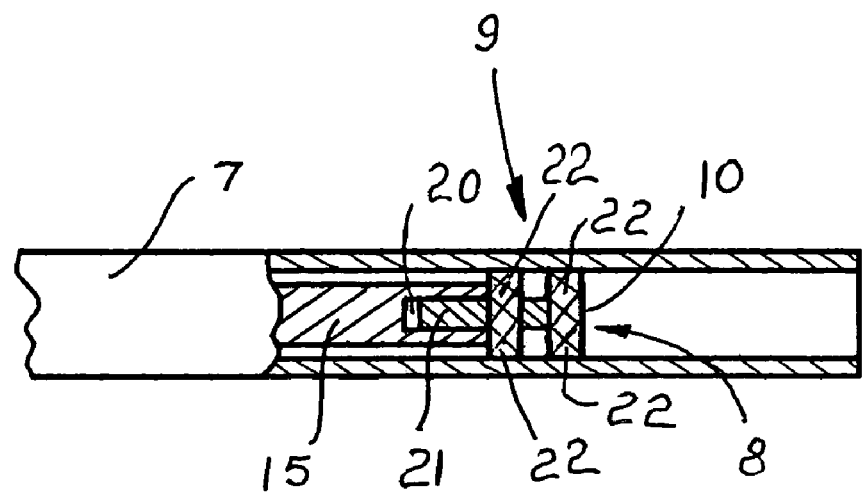
FIGS. 4a, 4b are the simplified drawing of the syringing portion.
Figure 4B:
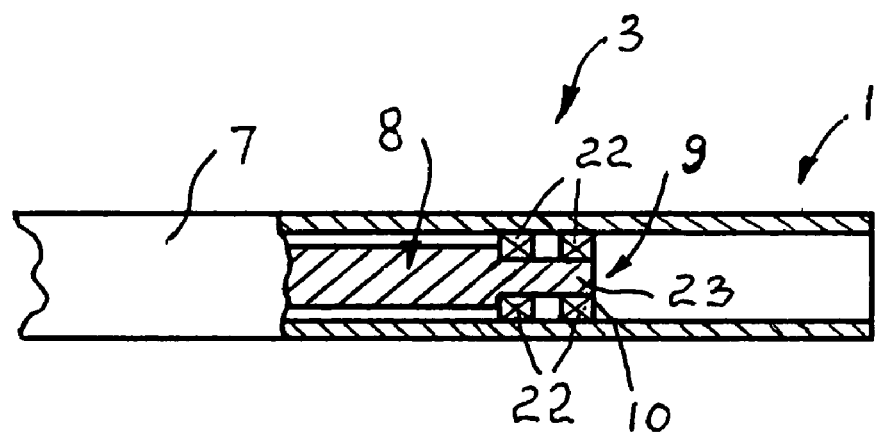

The piston member 9 of the piston portion 8 is rigidly connected (e.g. glued by non-toxic glue, etc.) to the connecting rod 15. The connection is provided by the deep 20 into connecting rod 15 and piston projection 21 of the piston member 9. The piston projection 21 and piston 22 can be made of the solid (entire) piece of material representing the piston member 9 (see FIG. 4*a*), or can be made of two separate pieces connected to each other (not shown). Also, as it is shown in FIG. 4*b*, the piston 22 can be put on the connecting rod projection 23.

The attachment portion 27 can be presented by a separate pipette/dropper 32 (partly shown in FIG. 5) with the nozzle 33 and a cover 28 comprising an aperture 29. The inner diameter of the cover 28 is slightly bigger than the outer diameter of the cylinder (barrel) 7.

The improved apparatus for dental implant treatment is used as following. The initial procedure is generally known and includes the following steps. The dental surgeon commences the procedure of replacing a deteriorated tooth with an artificial tooth by extracting the appropriate root or roots of the affected tooth or teeth in the common manner (e.g., full thickness mucoperiosteal flaps with bilateral vertical released incisions if necessary). The procedure may be utilized on either the mandible or the maxilla teeth and/or roots. The extraction of the root will cause the alveolar bone marrow to bleed through a resulting root extraction socket. The dental surgeon then performs vigorous debridment and suction of the root extraction socket to remove all infectious and periodontal membrane remnance, and as known to stimulate marrow bleeding from the socket.

Figure 5:
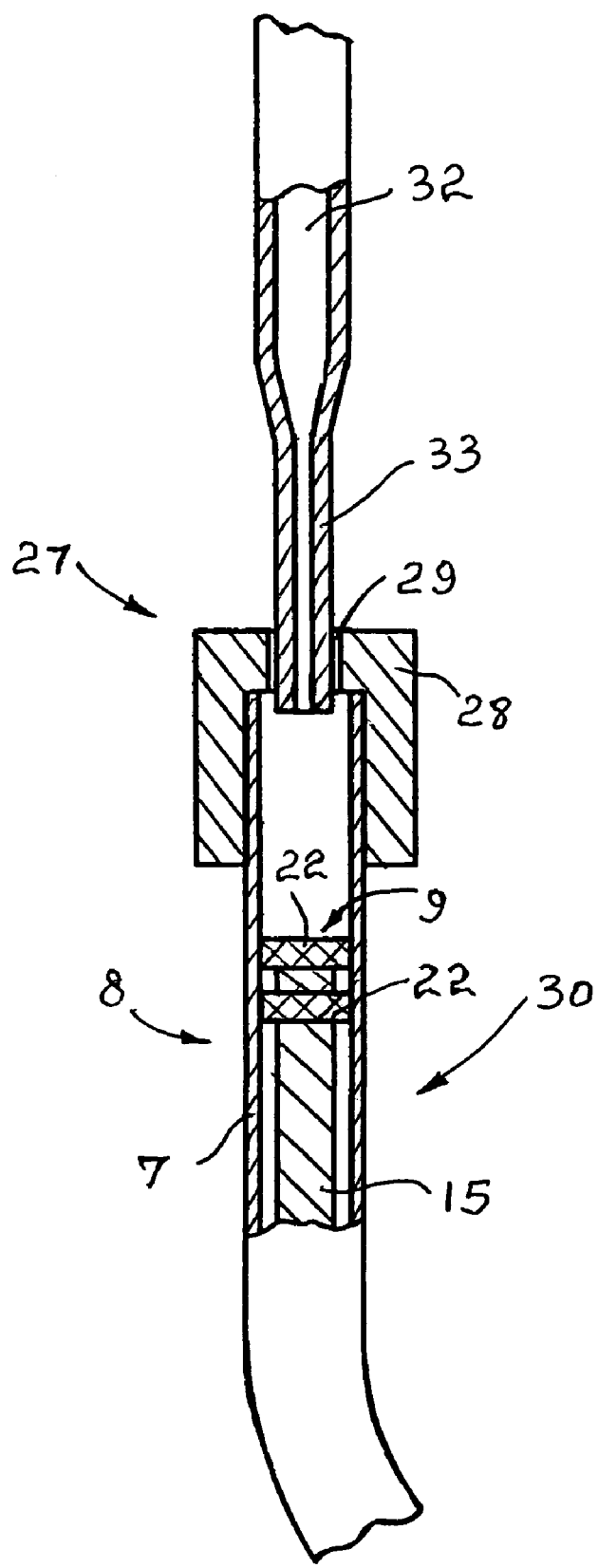
FIG. 5 is a simplified drawing of the attachment portion.

The dental surgeon preferably thereafter, in accordance with the known methods in the art, utilizes a dental handpiece and a bone drill to drill an appropriate hole (approximately 3 mm–6 mm of the depth) apically to the root extraction socket. The hole promotes marrow bleeding in the root extraction socket and serves as an extension of the root extraction socket into which a dental implant is secured. The blood from the surgical area of the patient's alveolar marrow is used to wet the HTR.RTM. (granulated synthetic bone pieces each is approximately of 750 micron diameter) or other graft material (e.g. such as Bioglass.RTM., Osteograf.RTM., Oestrogen.RTM., etc.) utilized. Further the dental surgeon uses the mentioned above pipette/dropper 32 collecting (sucking through the nozzle 33) the patient's blood from the tooth extracted socket (not shown) and through the aperture 29 into the cover 28 of the attachment portion 27 injects the blood from the pipette 32 into barrel (cylinder) 7 holding the syringe 30 in the manner, when the syringing side portion 3 is positioned up (the syringe 30 is positioned along longitudinal axis 16 with the syringing side portion 3 up and handle side portion 2 down), as shown in FIG. 5. Such position of the syringe 30 provides the best penetration of the blood into the cylinder 7 and the best absorption of the blood by the synthetic bone graft material 31 housed inside cylinder 7 at the syringing side portion 3 of the barrel portion 1.

According to the known procedure, the dental surgeon thereafter allows the blood wetted the synthetic bone graft material 31 to congeal approximately for a couple of minutes at the conclusion of which time he removes the cover 28 and injects the mixture of the patient's blood with the synthetic bone granules (a.k.a. bioactive bone grafting particulates) 31 into socket around the before installed dental implant (as has been mentioned above, the dental implant can be installed into socket after the synthetic bone graft material 31). The cover 28 can include filter, providing filtration of the injecting blood from microscopical debris into the blood for better blood absorption by the synthetic bones 31.

Thus, the described invention presents the improved not expensive apparatus for dental implant treatment, providing convenient and reliable injection of the synthetic bones during dental implant(s) installation procedure.

All means, components, portions, members, etc. described herein can be of any reasonable geometrical forms and configurations, can be of any reasonable size, color, etc., and can be of any non-toxic, sterile material (this description is not related to the HTR.RTM. material).

It should be understood that numerous modifications and variations of the present invention are possible in light of the above teachings and it is also understood that the above description discloses specific embodiments of the present invention and are for purposes of illustration only without any limitations. There may be other modifications and changes obvious to those of ordinary skill in the art which fall within the scope of the present invention and within scope of the appended claims, the invention may be practiced otherwise than as specifically described herein.

CONCLUSION, RAMIFICATION AND SCOPE

Accordingly the reader will see that, according to the invention, I have provided the improved apparatus for dental implant treatment. The improved apparatus for dental implant treatment has various possibilities, considering dental practice.

While the above description contains many specificities, these should be not construed as limitations on the scope of the invention, but as exemplification of the presently-preferred embodiments thereof. Many other ramifications are possible within the teaching to the invention. For example, the improved syringe of the improved apparatus for dental implant treatment can be successfully used in the periodontal cure and procedure, and/or during occlusion and bite registration procedures.

THE DRAWING REFERENCE NUMERALS

1.—a barrel portion;
2.—a handle side portion of the barrel;
3.—a syringing side portion of the barrel;
4.—a lateral axis;
5.—an end of the handle side portion;
6.—a rim;
7.—a cylinder (barrel);
8.—a piston portion;
9.—a piston member;
10.—a first end of the piston portion;
11.—a handle member;
12.—a second end of the piston portion;
13.—a finger rest;
14.—an adjustment means;
15.—a connecting rod;
16.—a longitudinal axis;
17.—a threaded portion;
18.—an outer thread;
19.—an inner thread;
20.—a deep;

21.—a piston projection;
22.—a piston;
23.—a connecting rod projection;
24.—a controlling means;
25.—a texture;
26.—an outer surface of the controlling means 24;
27.—an attachment portion;
28.—a cover;
29.—an aperture;
30.—a syringe;
31—a synthetic bone graft material;
32.—a pipette;
33.—a nozzle.

What is claimed is:

1. An improved apparatus for dental implant treatment comprising
    a syringe containing a synthetic bone graft material, having a lateral axis, and including
        a barrel portion comprising
            a cylinder including a handle side portion located at a first end of said barrel portion and a syringing side portion located at a second end of said barrel portion, wherein said cylinder is bent relative to the lateral axis at an angle of approximately 50°–70° at an area of said syringing side portion of said cylinder, and wherein said synthetic bone graft material is located at said syringing side portion;
            a rim perpendicularly extended from said cylinder at said first end of said barrel portion;
        a piston portion of said syringe including
            a connecting rod comprising a threaded portion located at an appropriate first end of said connecting rod, and wherein said threaded portion includes an outer thread;
            a finger rest perpendicularly extended from said appropriate first end of said connecting rod;
            an adjustment means including a controlling means comprising
                an inner thread compatible to said outer thread of said threaded portion of said connecting rod, and wherein said controlling means is coupled with said threaded portion of said connecting rod;
                a texture located on an outer surface of said controlling means;
            a piston member located at an appropriate second end of said connecting rod and including a piston rigidly connected to said connecting rod at said appropriate second end, and wherein said connecting rod is rigidly coupling said finger rest with said piston of said piston member;
        a cover coupled with said second end of said cylinder of said barrel portion overlapping said second end, and wherein said cover includes an aperture;
        a separate pipette providing injection of a dental patient's blood into said cylinder at said syringing side portion where is located said synthetic bone graft material, and wherein the injection of said dental patient's blood into said syringe is provided through said aperture of said cover.

2. The apparatus of claim 1, wherein said finger rest is further connected to said connecting rod.

3. The apparatus of claim 1, wherein said rim is further connected to said cylinder.

* * * * *